United States Patent
Liu et al.

(10) Patent No.: US 12,285,283 B2
(45) Date of Patent: Apr. 29, 2025

(54) SYSTEMS AND METHODS FOR MEDICAL IMAGE FUSION

(71) Applicant: Shanghai United Imaging Intelligence Co., Ltd., Shanghai (CN)

(72) Inventors: Yikang Liu, Cambridge, MA (US);
Zhang Chen, Brookline, MA (US);
Xiao Chen, Lexington, MA (US);
Shanhui Sun, Lexington, MA (US);
Terrence Chen, Lexington, MA (US)

(73) Assignee: Shanghai United Imaging Intelligence Co., Ltd., Shanghai (CN)

( * ) Notice: Subject to any disclaimer, the term of this patent is extended or adjusted under 35 U.S.C. 154(b) by 364 days.

(21) Appl. No.: 17/948,822

(22) Filed: Sep. 20, 2022

(65) Prior Publication Data

US 2024/0090859 A1   Mar. 21, 2024

(51) Int. Cl.
*A61B 6/00* (2024.01)
*A61B 6/50* (2024.01)

(52) U.S. Cl.
CPC .............. *A61B 6/487* (2013.01); *A61B 6/504* (2013.01)

(58) Field of Classification Search
CPC ......... A61B 6/481; A61B 6/487; A61B 6/504; G06N 3/0455; G06N 3/0464; G06N 3/084; G06T 7/0012; G16H 20/40; G16H 30/40; G16H 50/20; G16H 50/50
See application file for complete search history.

(56) References Cited

U.S. PATENT DOCUMENTS

| | | | |
|---|---|---|---|
| 6,351,513 B1 | 2/2002 | Bani-Hashemi et al. | |
| 6,389,104 B1 | 5/2002 | Bani-Hashemi et al. | |
| 8,298,147 B2 | 10/2012 | Huennekens et al. | |
| 10,893,843 B2 | 1/2021 | Kedmi-Shahar et al. | |
| 2006/0184006 A1* | 8/2006 | Chen ..................... | A61B 90/36 600/416 |
| 2007/0270689 A1 | 11/2007 | Lothert | |
| 2008/0275467 A1* | 11/2008 | Liao ..................... | A61B 90/36 703/11 |

(Continued)

FOREIGN PATENT DOCUMENTS

WO   2005004724 A1   1/2005

OTHER PUBLICATIONS

Daniel Toth et al., "3D/2D Registration with superabundant vessel reconstruction for cardiac resynchronization therapy," Aug. 5, 2017, Medical Image Analysis 42 (2017), pp. 160-171.*

(Continued)

*Primary Examiner* — Omar S Ismail
(74) *Attorney, Agent, or Firm* — Zhong Law, LLC

(57) ABSTRACT

A 3D anatomical model of one or more blood vessels of a patient may be obtained using CT angiography, while a 2D image of the blood vessels may be obtained based on fluoroscopy. The 3D model may be registered with the 2D image based on a contrast injection site identified on the 3D model and/or in the 2D image. A fused image may then be created to depict the overlaid 3D model and 2D image, for example, on a monitor or through a virtual reality headset. The injection site may be determined automatically or based on a user input that may include a bounding box drawn around the injection site on the 3D model, a selection of an automatically segmented area in the 3D model, etc.

20 Claims, 6 Drawing Sheets

(56) References Cited

U.S. PATENT DOCUMENTS

| | | | |
|---|---|---|---|
| 2009/0088830 A1* | 4/2009 | Mohamed | A61B 6/4423 |
| | | | 623/1.11 |
| 2013/0030295 A1 | 1/2013 | Huennekens et al. | |
| 2015/0351712 A1* | 12/2015 | Ohishi | A61B 6/504 |
| | | | 378/62 |
| 2016/0038246 A1* | 2/2016 | Wang | A61B 6/504 |
| | | | 600/587 |
| 2016/0302747 A1* | 10/2016 | Averbuch | A61B 6/5235 |
| 2017/0151027 A1* | 6/2017 | Walker | A61B 34/37 |
| 2018/0263706 A1* | 9/2018 | Averbuch | A61B 6/469 |
| 2019/0318476 A1* | 10/2019 | Isgum | A61B 6/507 |
| 2022/0343567 A1* | 10/2022 | O'Connor | G06T 11/008 |

OTHER PUBLICATIONS

Peter Mountney et al., "A Planning and Guidance Platform for Cardiac Resynchronization Therapy," Oct. 25, 2017, IEEE Transactions on Medical Imaging, vol. 36, No. 11, Nov. 2017, pp. 2366-2374.*

Hélène Langet, "Sampling and Motion Reconstruction in Three-dimensional X-ray Interventional Imaging," Nov. 18, 2013, HAL theses, pp. 7-53.*

Shun Miao et al., "Toward smart utilization of two X-ray images for 2-D/3-D registration applied to abdominal aortic aneurysm interventions," Jan. 30, 2013, Computers and Electrical Engineering 39 (2013), pp. 1485-1495.*

* cited by examiner

SYSTEMS AND METHODS FOR MEDICAL IMAGE FUSION

BACKGROUND

Medical imaging such as X-ray fluoroscopy may be used in surgical procedures, for example, to guide the insertion or implantation of interventional devices into a human body in real time. To visualize the devices and/or human organs (e.g., blood vessels) involved in these procedures, radiopaque contrast agents may be injected into the blood vessels of the patient such that the devices and/or blood vessels may be delineated from other background objects in the images captured by a medical imaging device (e.g., such as a computed tomography (CT) scanner or an X-ray scanner). Currently available imaging technologies and contrast agents, however, may cause potential adverse effects on the human body and, as such, imaging procedures need to be completed quickly since the contrast agents may need to be washed out soon after injection and/or be kept at a lower dosage in order to avoid the adverse effects. These constraints may limit a clinician's ability to monitor the implantation of medical devices during surgical procedures, and may affect the speed and success rate of those procedures.

SUMMARY

Described herein are systems, methods, and instrumentalities associated with medical image registration and fusion. An apparatus capable of performing such a task may include at least one processor configured to obtain a three-dimensional (3D) anatomical model representing one or more blood vessels of a patient, and a two-dimensional (2D) fluoroscopic image of all or a subset of the one or more blood vessels, where the 2D fluoroscopic image may indicate that at least one of the one or more blood vessels is injected with a contrast agent (e.g., contrast dye). The at least one processor may be further configured to determine an injection site of the contrast agent in the 2D fluoroscopic image and on the 3D anatomical model (e.g., automatically or based on a user input), and register the 3D anatomical model with the 2D fluoroscopic image based at least on respective locations of the injection site in the 2D fluoroscopic image and the 3D anatomical model such that the 3D anatomical model aligns (e.g., approximately) with the 2D fluoroscopic image with respect to at least one of the one or more blood vessels. The at least one processor may also be configured to overlay (e.g., project) the 3D anatomical model onto the 2D fluoroscopic image, and generate an image that depicts the overlaid 3D anatomical model and the 2D fluoroscopic image. The image may then be displayed on a monitor or through a virtual reality (VR) headset, either or both of which may also be parts of the apparatus, such that the overlaid 3D blood vessel model and the 2D fluoroscopic image may be visualized on the monitor or through the VR headset.

In embodiments, the at least one processor of the apparatus may be configured to determine the injection site on the 3D anatomical model based on a user input that may indicate the location of the injection site on the 3D anatomical model. Such a user input may comprise, for example, a bounding box drawn on the 3D anatomical model that may mark the injection site. In embodiments, the at least one processor of the apparatus may be configured to determine the injection site on the 3D anatomical model by performing at least the following. The processor may segment the 3D anatomical model into multiple segments, each of which may represent an anatomical structure of the patient. The processor may further receive a user input that may indicate which one or more of the multiple segments include the injection site, and determine the injection site based on the user input.

In embodiments, the 2D fluoroscopic image may be obtained using a medical imaging device such as a C-arm X-ray machine, and the at least one processor may be configured to determine the injection site on the 3D anatomical model by performing at least the following. The processor may determine the position and body shape of the patient based on information provided by a sensing device (e.g., a camera configured to capture pictures of the patient). The processor may further determine the relative positions and orientations of the 3D anatomical model and the sensing device as well as the relative positions and orientations of the medical imaging device and the sensing device, and determine the injection site on the 3D anatomical model based at least on the position or body shape of the patient, the relative positions and orientations of the 3D anatomical model and the sensing device, and the relative positions and orientations of the medical imaging device and the sensing device.

In embodiments, the at least one processor of the apparatus may also be configured to generate, based on the 2D fluoroscopic image, a 2D mask associated with the one or more blood vessels of the patient, and register the 2D mask with the 3D anatomical model based on the injection site. In embodiments, the at least one processor may be further configured to detect, based on the 2D fluoroscopic image, a medical device implanted inside one of the one or more blood vessels of the patient, generate a 3D model of the medical device based on a predefined device model, and overlay the 3D model of the medical device onto a 3D image that depicts the blood vessel in which the medical device is implanted. Such a 3D image may be the image used to obtain the 3D anatomical model, or a 3D image that is registered with the image used to obtain the 3D anatomical model.

BRIEF DESCRIPTION OF THE DRAWINGS

A more detailed understanding of the examples disclosed herein may be obtained from the following description, given by way of example in conjunction with the accompanying drawings.

DETAILED DESCRIPTION

The present disclosure is illustrated by way of example, and not by way of limitation, in the figures of the accompanying drawings. A detailed description of illustrative embodiments will now be described with reference to the various figures. Although this description provides a detailed example of possible implementations, it should be noted that the details are intended to be exemplary and in no way limit the scope of the application.

Figure 1:
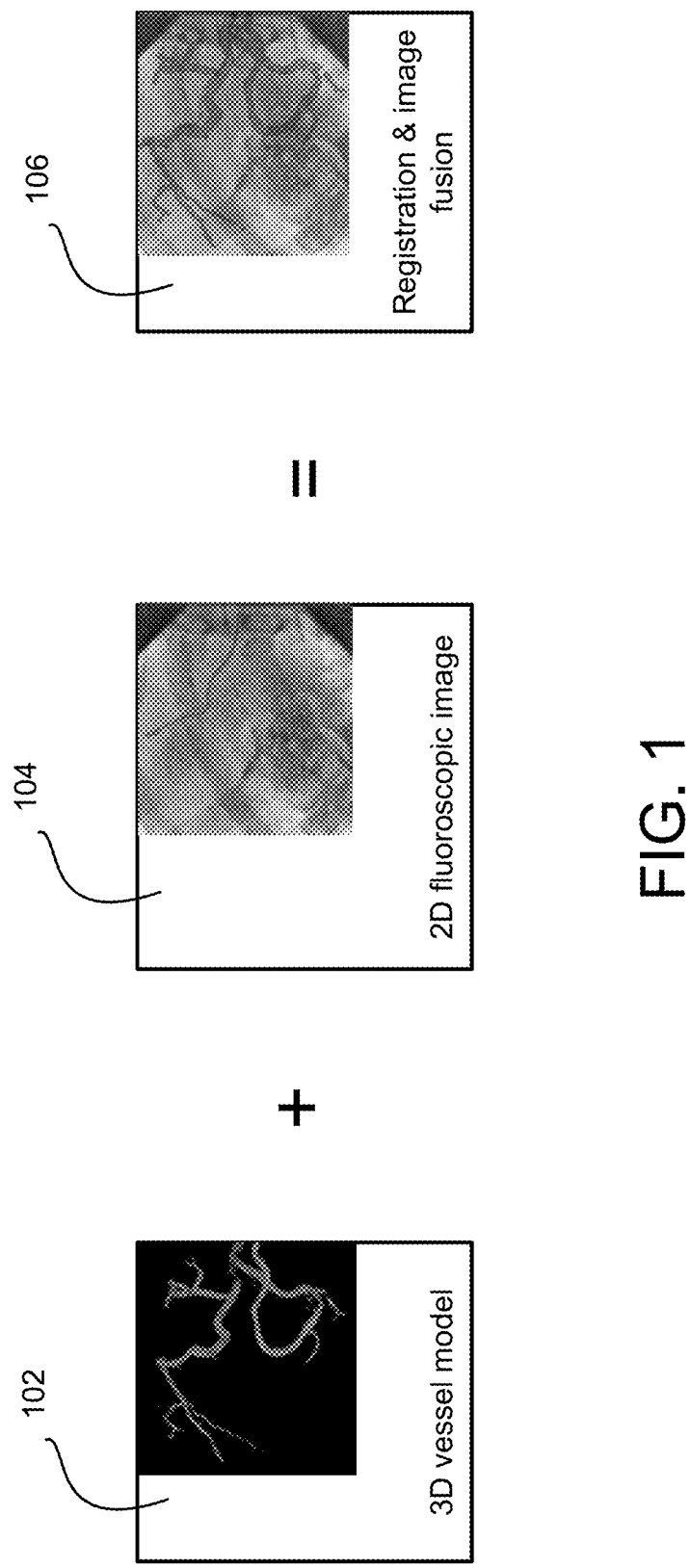
FIG. 1 is a simplified diagram illustrating an example process for registering and/or fusing medical images, according to some embodiments described herein.

FIG. 1 illustrates an example process for registering and/or fusing medical images in accordance with one or more embodiments described herein. The medical images may include various types of two-dimensional (2D) or three-dimensional (3D) images (including 3D models), and may depict various anatomical structures of a human body and/or medical devices implanted into the human body. For instance, the medical images may depict one or more blood vessels such as coronary arteries or veins, one or more implantable devices such as catheters or stents, and/or the like. The medical images (including 3D models) may be obtained using various medical imaging and modeling technologies. For instance, the medical images may include a 3D anatomical model 102 (e.g., a 3D vessel model or image) obtained based on computed tomography (CT) angiography, and a 2D medical image 104 (e.g., a fluoroscopic image) obtained based on X-ray fluoroscopy. The 3D anatomical model 102 may represent one or more blood vessels of a patient (e.g., the model may also include other anatomical structures such as bones and/or joints of the patient), while the 2D medical image 104 may be an image of all or a subset of the one or more blood vessels represented by the 3D model.

In embodiments of the present disclosure, the 3D model 102 may be obtained during a preoperative step, e.g., before a surgical procedure is started for the patient, while the 2D medical image 104 may be obtained during the surgical procedure, e.g., after injecting a contrast agent (e.g., a contrast dye) into one or more blood vessels of the patient that are represented by the 3D anatomical model 102. Once obtained, the 2D medical image 104 may be registered with the 3D model 102 such that at least one of the blood vessels on the 3D anatomical model 102 may be aligned (e.g., approximately) with the at least one of the blood vessels on the 2D medical image 104. The registered 3D anatomical model 102 and 2D medical image 104 may then be fused together, for example, by overlaying (e.g., projecting) the 3D anatomical model 102 onto the 2D medical image 104, and generating an image 106 that depicts the overlaid 3D anatomical model 102 and the 2D medical image 104. The fused image 106 may be used for various purposes. For example, since the 2D medical image 104 may be an image captured with contrast, the image may show which specific blood vessel has been injected with a contrast agent, the position of the contrast agent inside the blood vessel, the position of an implanted medical device (e.g., a catheter) inside the blood vessel, etc. Thus, by capturing multiple of these images, and registering/fusing them with the 3D anatomical model 102, a clinician may be able to monitor the placement and movements of the contrast agent and/or the implanted medical device inside the patient's body (e.g., against the 3D anatomical model) to ensure that the medical device is being placed properly.

In embodiments of the present disclosure, the fused image 106 (e.g., multiple such fused images) may be displayed (e.g., played back as an animation or movie) on a monitoring device such as a computer monitor and/or a virtual reality (VR) headset. In embodiments of the present disclosure, a 2D vessel mask may be obtained based on the 2D medical image 104 (e.g., using a pre-trained artificial intelligence (AI) segmentation model) and registered/fused with the 3D anatomical model (e.g., in addition to or instead of registering the 2D medical image 104 with the 3D anatomical model 102) to facilitate one or more clinical tasks. In embodiments of the present disclosure, a 3D model of the implanted medical devices may be reconstructed based on the 2D medical image 104 and/or a pre-defined device model for the implanted medical device. The 3D device model may then be overlaid with a 3D medical image of the anatomical structure in which the medical device is implanted to depict the position and/or orientation of the implanted medical device in the anatomical structure. The 3D medical image on which the 3D device model is overlaid may be the image used to generate the 3D anatomical model 102 or another image that is registered to the image used to generate the 3D anatomical model 102.

The registration of the 3D anatomical model 102 and the 2D medical image 104 may be accomplished automatically (e.g., based on a pre-trained AI image registration model) and/or based on a user input that may assist with the registration. For example, an interface (e.g., a graphical user interface) may be provided to the user, through which the 2D medical image 104 may be displayed and the user may identify at least one blood vessel in the 2D medical image that may have been injected with a contrast agent. Responsive to identifying such a blood vessel in the 2D medical image 104, the user may indicate, in the 2D medical image 104 and/or on the 3D anatomical model 102, a location of the contrast injection site (e.g., the location of a catheter tip when injecting the contrast agent) and/or at least one blood vessel associated with the injection site. The user may, for example, provide the indication by clicking or drawing a bounding box around a specific area of the 2D medical image 104 and/or the 3D anatomical model 102 to mark up the injection site. The injection site may then be used as reference landmarks or features to improve the accuracy of the registration and/or to reduce the computation involved with the registration. In embodiments of the present disclosure, using a pre-trained AI segmentation model, the 2D medical image 104 and/or the 3D anatomical model 102 may be automatically segmented into multiple segments, and key landmarks may be automatically labeled (e.g., to indicate femoral bifurcation, common femoral arteries, common iliac arteries, abdominal aorta, left ventricle, etc.). The user may then select one of the segments and/or key landmarks to indicate that the selected segment or landmark includes the injection site or the blood vessel associated with the injection site.

In embodiments of the present disclosure, sensing devices such as digital cameras, depth sensors, thermal sensors, and/or radar sensors may be set up in an operating room and used to capture images (e.g., color image, depth images, etc.) of the patient. The patient images may then be used to construct a human model (e.g., a 3D body mesh) that may represent the position, pose, and/or body shape of the patient at the time the 2D medical image 104 is captured. Based on the position, pose, and/or body shape of the patient represented by the 3D human model, the relative positions and orientations of the 3D anatomical model and the sensing device, and the relative positions and/or orientations of the sensing device and the medical scanner (e.g., a C-arm X-ray machine) used to capture the 2D medical image 104, the location of the injection site described herein may be automatically determined on the 3D anatomical model 102 and used to facilitate (e.g., refine) the registration of the 3D anatomical model 102 and the 2D medical image 104. In examples, the CT images that are used to generate the 3D anatomical model 102 may be registered with the human model (e.g., the 3D body mesh) to improve the accuracy of the injection site determination.

Figure 2:
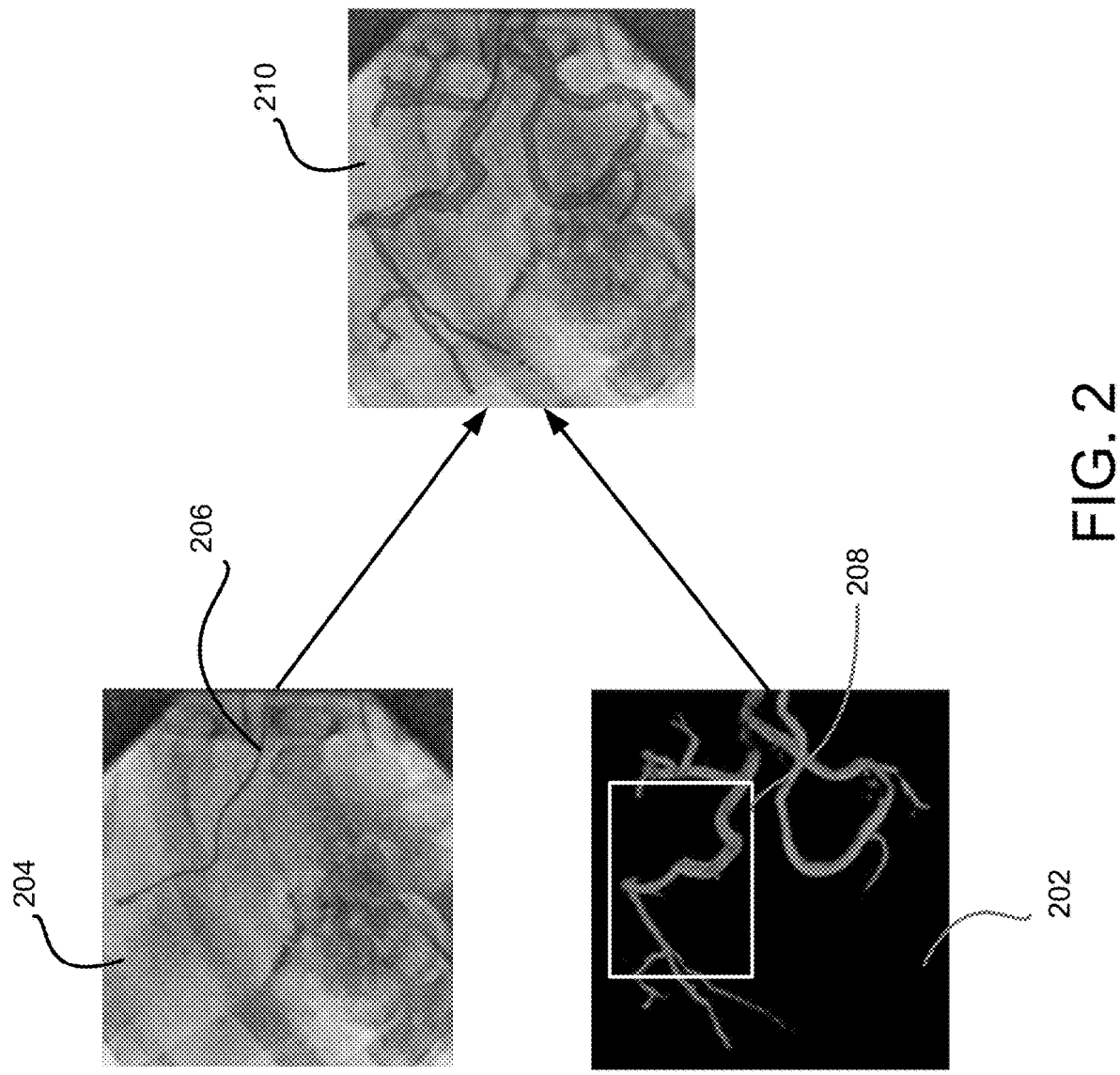
FIG. 2 is a simplified diagram illustrating an example of registering and/or fusing a 3D anatomical model with a 2D fluoroscopic image, according to some embodiments described herein.

FIG. 2 illustrates an example of registering and/or fusing a 3D anatomical model 202 (e.g., the anatomical model 102 of FIG. 1) with a 2D fluoroscopic image 204 (e.g., the 2D medical image 104 of FIG. 1) in accordance with one or more embodiments of the present disclosure. As shown, the registration and/or fusion may be facilitated by a user input that may indicate where a contrast injection site (e.g., the location of a catheter insertion) is in the 2D fluoroscopic image 204 and/or on the 3D anatomical model 202. The user input may be provided by the user based on the 2D fluoroscopic image 204. For example, an interface (e.g., a graphical user interface) may be provided, through which the 2D fluoroscopic image 204 may be displayed and the user may identify and/or indicate (e.g., based on the contrast reflected through the 2D fluoroscopic image) at least one blood vessel 206 that may be injected with a contrast agent (e.g., contrast dye). Responsive to identifying such a blood vessel 206 based on the 2D fluoroscopic image 204, the user may (e.g., using the same interface) indicate, in the 2D fluoroscopic image 204 and/or on the 3D anatomical model, a location of the contrast injection site (e.g., a catheter tip) and/or at least one blood vessel associated with the contrast injection. As shown in the example of FIG. 2, the user may do so by drawing a bounding box 208 around a specific area of the 3D anatomical model 202 (and/or in the 2D fluoroscopic image 204) to indicate the location of the injection site and/or the blood vessel associated with the injection site. In some examples, the 3D anatomical model 202 and/or the 2D fluoroscopic image 204 may be automatically segmented into multiple segments, and key landmarks may be automatically labeled (e.g., using a pre-trained AI model), such that the user may select one of the segments and/or key landmarks to indicate that the selected segment or landmark includes the injection site or the blood vessel associated with the injection site.

The injection site and/or blood vessel determined based on the user input may be used as reference landmarks or features to facilitate (e.g., refine) the registration and/or fusion 210 of the 3D anatomical model 202 and 2D fluoroscopic image 204. For example, the problem of image registration may be formulated as finding a geometrical transformation $T:I_F \rightarrow I_M$ to align a moving image $I_M$ to a fixed image $I_F$. This alignment may be achieved by optimizing a similarity measure L (e.g., a loss function) based on feature correspondences (e.g., lines, corners, contours etc.) between the fixed and moving images. As such, by determining the injection site and/or blood vessel associated with the injection site on the 3D anatomical model 202 (e.g., which may be deemed a 3D image) and the 2D fluoroscopic image 204, peer features on the two images may be detected (e.g., learned using a deep neural network) more quickly and accurately, leading to improved alignment of the peer features (e.g., through translation, rotation, scaling, etc.) and better results for the image registration/fusion.

Figure 3:
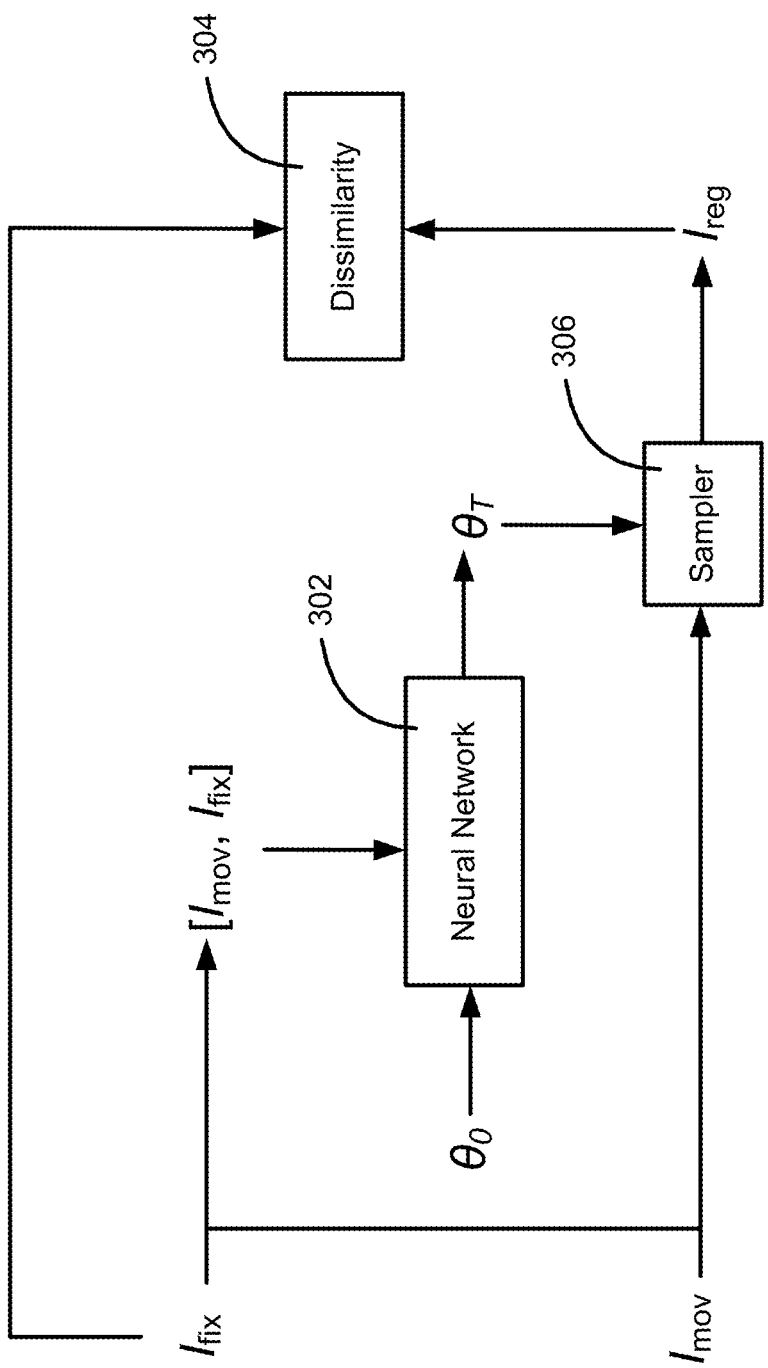
FIG. 3 is a simplified diagram illustrating an example of registering two images using an artificial neural network (ANN), according to some embodiments described herein.

FIG. 3 illustrates an example of registering two images, $I_{mov}$ (e.g., a source image) and $I_{fix}$ (e.g., a target image such as the 3D anatomical model 202 of FIG. 2), using an artificial neural network (ANN) 302. One of the images $I_{fix}$ and $I_{mov}$ may be a 2D medical image such as the 2D medical image 104 of FIG. 1 or 204 of FIG. 2, while the other one of the images $I_{fix}$ and $I_{mov}$ may be a 3D image such as the 3D anatomical model 102 of FIG. 1 or 202 of FIG. 2. The neural network 302 may be configured to receive the images $I_{fix}$ and $I_{mov}$ (e.g., as inputs), transform the image $I_{mov}$ from a moving image domain (e.g., associated with the image $I_{mov}$) to a fixed image domain (e.g., associated with the image $I_{fix}$), and generate an image $I_{reg}$ (e.g., as a spatial transformed version of the image $I_{mov}$) that resembles the image $I_{fix}$ (e.g., with a minimized dissimilarity 304 measure between $I_{fix}$ and $I_{reg}$). The neural network 304 may be trained to determine a plurality of transformation parameters OT for transforming the image $I_{mov}$ into the image $I_{reg}$. This operation may be illustrated by the following:

$$I_{reg} = I_{mov}(\theta(x)) \qquad (1)$$

where x may represent coordinates in the moving image domain, θ(x) may represent the mapping of x to the fixed image domain, and $I_{mov}(\theta(x))$ may represent one or more grid sampling operations (e.g., using a sampler 306). θ may include parameters associated with an affine transformation model, which may allow for translation, rotation, scaling, and/or skew of the input image. θ may also include parameters associated with a deformable field (e.g., a dense deformation field), which may allow for deformation of the input image. For example, θ may include rigid parameters, B-spline control points, deformable parameters, and/or the like.

In embodiments of the present disclosure, the neural network 302 may be configured to determine values $θ_T$ of the transformation parameters based on a set of initial values $θ_0$ of the transformation parameters and an integral of updates (e.g., gradient updates) to the transformation parameters determined by the neural network 302. The initial values $θ_0$ of the transformation parameters may be obtained, for example, from a normal distribution (e.g., randomly), based on an existing image registration model, etc. In examples, the neural network 302 may include a neural ordinary differential equation (ODE) network configured to determine the transformation parameters $θ_T$ by solving an ordinary differential equation associated with the transformation parameters. Such a neural ODE network may include one or more ODE layers or ODE blocks, each of which may be configured to determine (e.g., predict or estimate) a respective update (e.g., gradient update) to the transformation parameters based on a present or current state (e.g., current values) of the transformation parameters. For example, the neural network 302 may be configured to determine respective updates to the transformation parameters through one or more iterations (e.g., through the one or more ODE layers or blocks), and each of the updates may be determined based on the present state of the transformation parameters associated with each of the one or more iterations. The updates may then be used to obtain (e.g., derive) final values $θ_T$ of the transformation parameters utilizing an ODE solver. For instance, the ODE solver may be used to integrate the respective updates (e.g., gradient updates) determined (e.g., predicted) by the one or more ODE layers or blocks, and apply the integral of the updates to the initial parameter values $θ_0$ to derive the final values $θ_T$.

The operation of the neural ODE network described above may be illustrated by the following. Formulating the image registration task as $$\theta_{opt} = \underset{\theta}{\mathrm{argmin}}\, C(\theta; I_{fix}, I_{mov}),$$

where θ may represent the transformation parameters described herein and C may represent a loss (or cost) function designed to indicate the dissimilarity 304 between $I_{fix}$ and $I_{mov}$ (θ(x)), the transformation parameters θ may be derived utilizing a gradient descent-based optimization technique, such as the one illustrated below:

$$\theta_{t+1} = \theta_t - \eta_t(\partial C/\partial \theta) \quad (2)$$

where t may represent an iteration in the optimization process, $\eta_t$ may represent an optimization step size, and ∂C/∂θ may represent a derivative of the loss function C at a current or present state $\theta_t$ (e.g., representing current values) of the transformation parameters.

The neural ODE network may be trained to predict an update (e.g., a gradient update) corresponding to $\eta_t(\partial C/\partial \theta)$ shown in Equation (2), and the update predicted by such a network may be represented as:

$$\theta_{t+1} = \theta_t + f(\theta_t, \mu_t) \quad (3)$$

where f may represent the neural ODE network parameterized with $\mu_t$. With a sufficiently small t, the updates may occur in a continuous manner (e.g., a substantially continuous manner), as represented by the following ordinary differential equation:

$$\frac{d\theta(t)}{dt} = f_\mu(\theta(t), t) \quad (4)$$

where $f_\mu$ may represent the neural ODE network parameterized with μ.

Hence, starting from the initial parameter values $\theta_0$, the neural ODE network may be trained to produce, e.g., utilizing an ODE solver, an output $\theta_T$ (e.g., final values of the transformation parameters) that corresponds to a solution to the ordinary differential equation shown in (4) (e.g., the function of the ODE network may be understood as solving an initial value problem during a time period of [0, T]). When the inputs to the neural ODE network include images such as images $I_{fix}$ and $I_{mov}$ shown in FIG. 3, a gradient update predicted by the neural ODE network (e.g., by a layer of the ODE network) may be represented as:

$$\frac{d\theta(t)}{dt} = f_\mu(I_{mov}(\theta_t(x)), I_{fix}, t) \quad (5)$$

and a solution to the ordinary differential equation may be:

$$\theta_T = \theta_{t0} + \int_{t0}^{T} f_\mu(I_{mov}(\theta_t(x)), I_{fix}, t) * dt \quad (6)$$

and $$\theta_{t+dt} = \theta_t + f_\mu(I_{mov}(\theta_t(x)), I_{fix}, t) * dt \quad (7)$$

where (6) may represent continuous derivation of the parameters at T and (7) may represent a step (e.g., from t to t+dt) in the derivation process.

Once the values of the transformation parameters $\theta_T$ are obtained, they may be used to transform the input image $I_{mov}$ to $I_{reg}$, for example, via one or more resampling operations that may be performed using the sampler 306. During training of the neural ODE network, the image Ire g may be compared to the input image $I_{fix}$ and the dissimilarity 304 between the two images may be determined based on a loss function (e.g., a loss function based on an Euclidean distance, a cross correlation, a normalized cross correlation, etc.). The dissimilarity 304 may then be used to guide the adjustment of the network parameters, for example, with an objective to minimize the dissimilarity 304.

Figure 4:
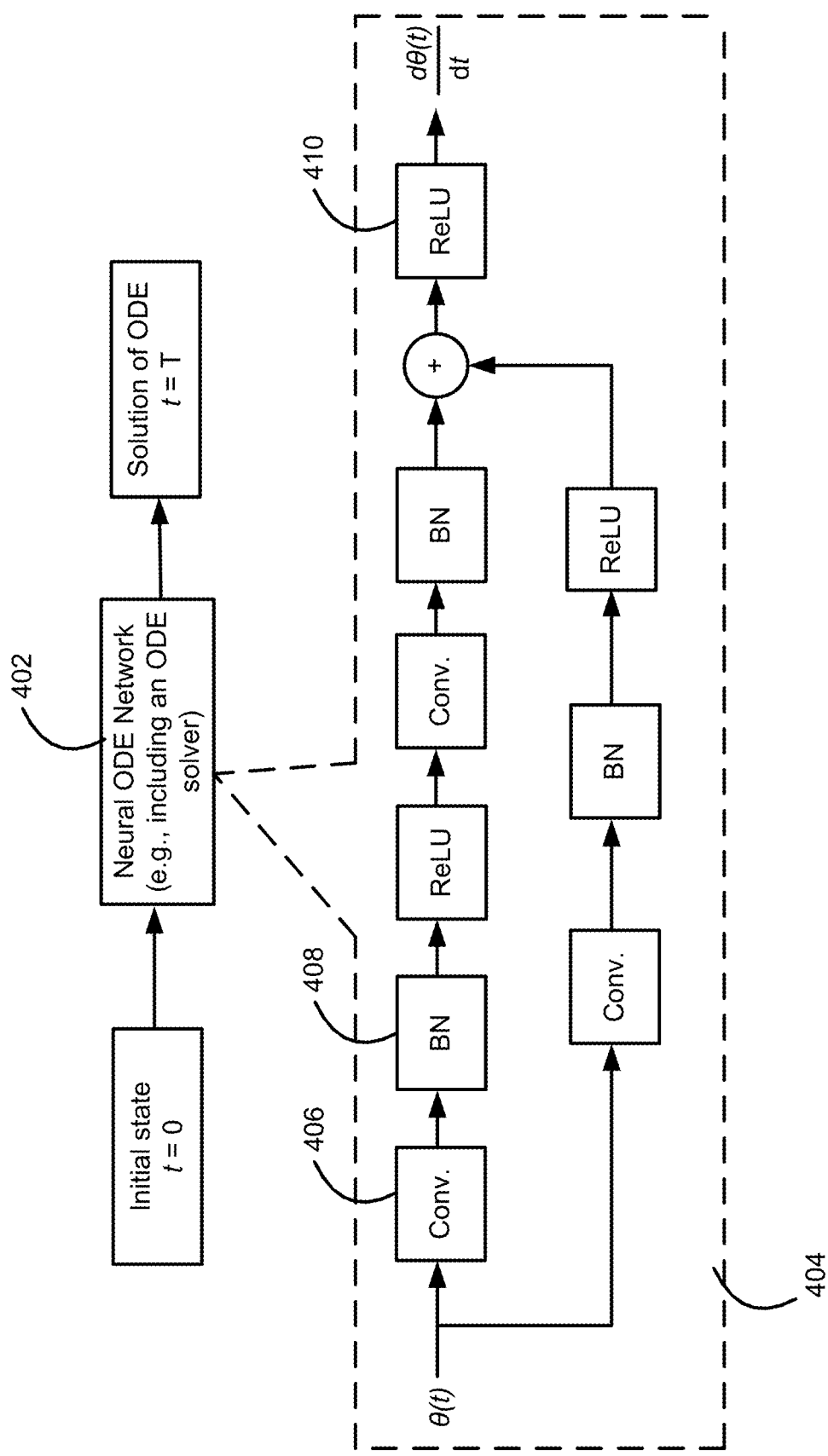
FIG. 4 is a simplified diagram illustrating an example structure of a neural ordinary differential equation (ODE) network that may be used to determine transformation parameters for registering two medical images, according to some embodiments described herein.

FIG. 4 shows an example structure of a neural ODE network 402 (e.g., the neural network 302 of FIG. 3) that may be configured to determine parameters (e.g., transformation parameters) for registering a first medical image with a second medical image. The figure shows one ODE layer or block 404 associated with one hidden state θ(t) of the transformation parameters, but a skilled person in the art will appreciate that the neural ODE network 402 may include multiple such layers or blocks and that the transformation parameters may adjusted through a series of transformations involving multiple hidden states. As shown in the figure, the ODE layer or block 404 may include one or more convolutional layers 406, one or more batch normalization (BN) layers 408, one or more activation functions 410 (e.g., rectified linear unit (ReLU) activation functions), one or more pooling layers (not shown), and/or one or more fully connected layers (not shown). Each of the convolutional layers 406 may include a plurality of convolution kernels or filters with respective weights configured to extract features from the image(s) received by the neural ODE network 402 (e.g., the source image $I_{mov}$ and/or target image $I_{fix}$ described herein). The operations of the convolutional layers 406 may be followed by batch normalization (BN) (e.g., via the BN layer 408) and/or linear or non-linear activation (e.g., using the ReLU 410), and the features extracted by the convolutional layers 406 may be down-sampled through a contraction path (e.g., comprising one or more pooling layers and/or one or more fully connected layers) to reduce the redundancy and/or dimension of the extracted features. In some examples, the down-sampled features may be subsequently processed through an expansive path (e.g., comprising one or more transposed convolutional layers and/or one or more un-pooling layers) during which the features may be up-sampled to a higher resolution.

The features extracted by the convolution operations described herein may be used by the neural ODE network 402 to determine transformation parameters for spatially aligning the images of interest. The neural ODE network 402 may predict the transformation parameters, for example, by continuously transforming the hidden state θ(t) of the parameters through one or more of the ODE layer or block 404. Each transformation may correspond to transforming the hidden state of the parameters from θ(t) to θ(t+Δt), where Δt may represent a transformation or optimization step or size. As Δt approaches zero (e.g., when the transformation step is sufficiently small), a final state of the transformation parameters (e.g., θ(t=T)) may be obtained by solving an ODE associated with the transformation parameters (e.g., as illustrated by Equations 4-7). The amount of transformation (e.g., adjustment), $$\frac{d\theta(t)}{dt},$$

determined and/or applied by the ODE block 404 may be evaluated using an ODE solver (e.g., as illustrated by Equation(s) 6 and/or 7 described herein) and the error tolerance level of the ODE solver may determine the number of transformations and/or evaluations to be performed before final values of the transformation parameters are obtained. The ODE solver may be implemented using various numerical analysis techniques. For example, the ODE solver may include an Euler solver (e.g., based on the Euler method for solving an ODE), a Runge-Kutta (RK) solver such as an RK2 or RK4 solver (e.g., based on a Runge-Kutta (RK) method for solving an ODE), an adaptive step size solver (e.g., based on an adaptive step size method for solving an ODE), etc. The ODE solver may be a stand-alone solver (e.g., separated from the neural ODE network 402) or may be part of the neural ODE network 402 (e.g., the ODE solver itself may be learned through training). The error tolerance level of the ODE solver may be configurable (e.g., as a hyper-parameter of the neural ODE network 402) and may be assigned the same value or different values for training and inference purposes.

The injection site indication described herein may be used to guide the feature extraction and/or transformation parameter determination process associated with image registration and/or fusion. For example, initial transformation parameter values $\theta_0$ for registering the 3D anatomical model and the 2D fluoroscopic image described herein may be determined based on the location of the injection site in the 2D fluoroscopic image, which may be determined using a convolutional neural network such as one having a U-shaped encoder-decoder architecture. The neural ODE network may be trained with a constraint loss, under which updated transformation parameters that stray far away from the initial transformation parameter values $\theta_0$ may be penalized.

Figure 5:
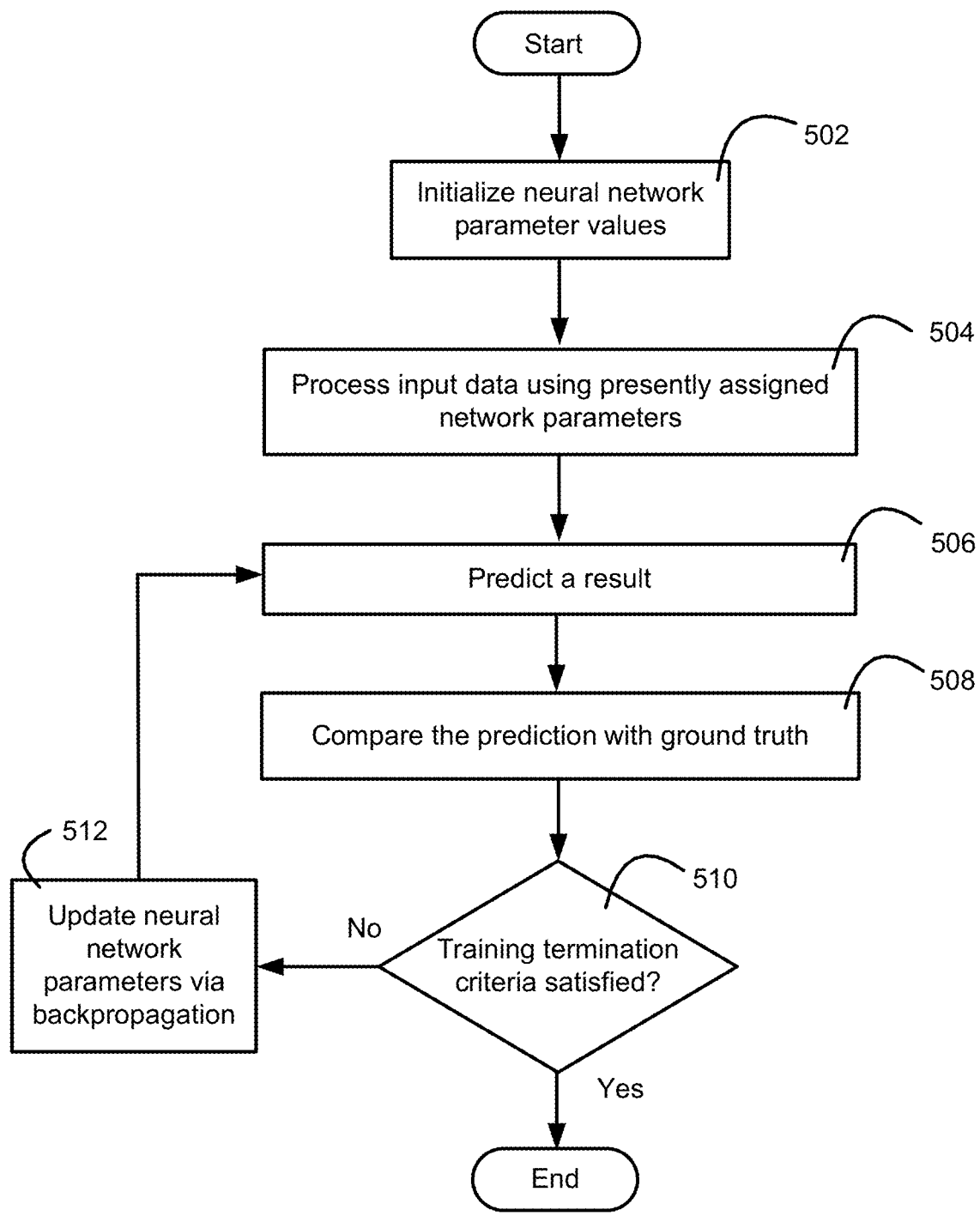
FIG. 5 is a flow diagram illustrating an example method for training a neural network to perform one or more of the tasks as described with respect to some embodiments provided herein.

FIG. 5 shows a flow diagram illustrating an example process 500 for training a neural network (e.g., an AI model implemented by the neural network) to perform one or more of the tasks described herein. As shown, the training process 500 may include initializing the operating parameters of the neural network (e.g., weights associated with various layers of the neural network) at 502, for example, by sampling from a probability distribution or by copying the parameters of another neural network having a similar structure. The training process 500 may further include processing an input (e.g., a training image) using presently assigned parameters of the neural network at 504, and making a prediction for a desired result (e.g., image transformation parameters) at 506. The prediction result may be compared to a ground truth at 508 to determine a loss associated with the prediction, for example, based on a loss function such as mean squared errors between the prediction result and the ground truth, an L1 norm, an L2 norm, etc. At 510, the loss may be used to determine whether one or more training termination criteria are satisfied. For example, the training termination criteria may be determined to be satisfied if the loss is below a threshold value or if the change in the loss between two training iterations falls below a threshold value. If the determination at 510 is that the termination criteria are satisfied, the training may end; otherwise, the presently assigned network parameters may be adjusted at 512, for example, by backpropagating a gradient descent of the loss function through the network before the training returns to 506.

For simplicity of explanation, the training steps are depicted and described herein with a specific order. It should be appreciated, however, that the training operations may occur in various orders, concurrently, and/or with other operations not presented or described herein. Furthermore, it should be noted that not all operations that may be included in the training method are depicted and described herein, and not all illustrated operations are required to be performed.

Figure 6:
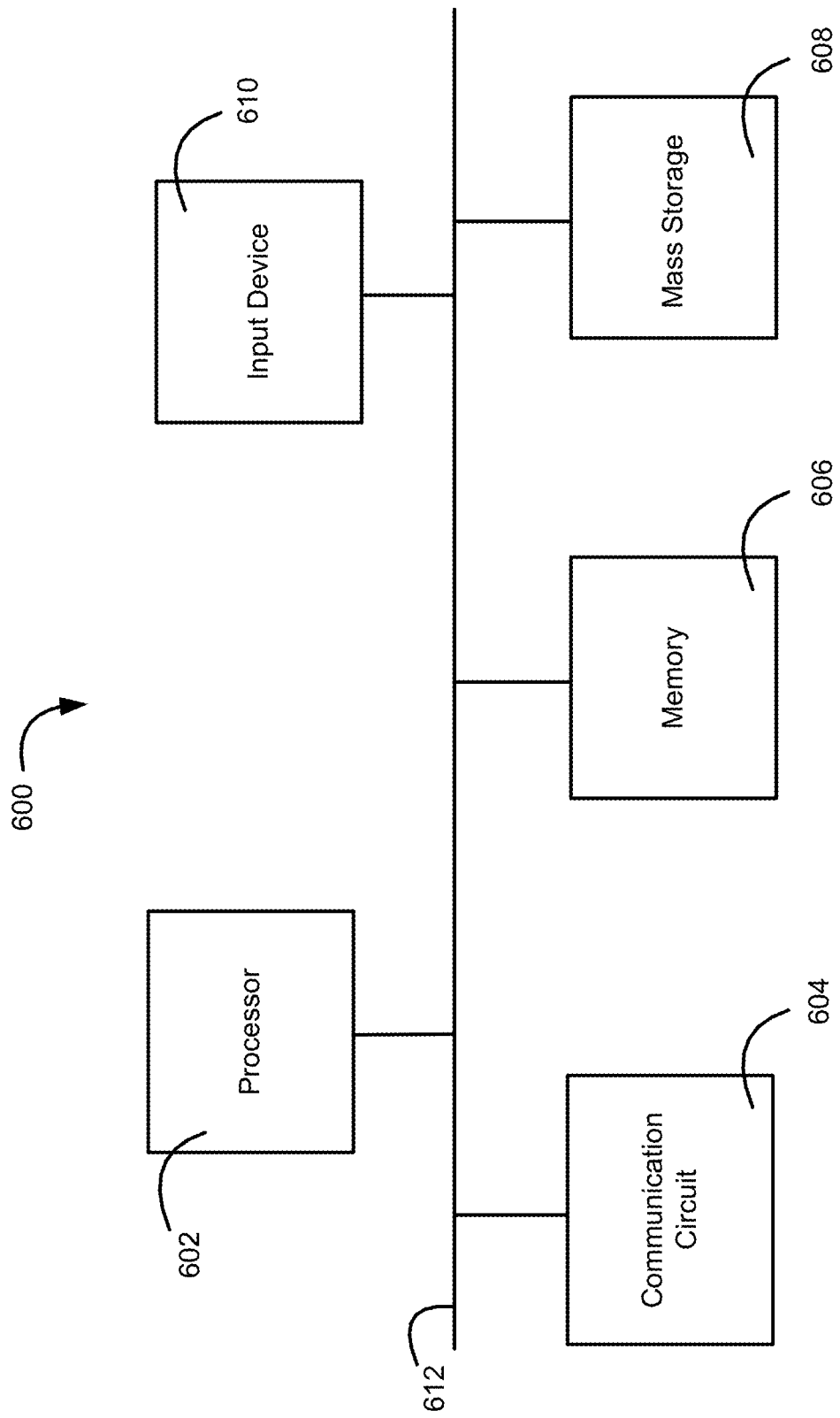
FIG. 6 is a simplified block diagram illustrating an example system or apparatus for performing one or more of the tasks as described with respect to some embodiments provided herein.

The systems, methods, and/or instrumentalities described herein may be implemented using one or more processors, one or more storage devices, and/or other suitable accessory devices such as display devices, communication devices, input/output devices, etc. FIG. 6 illustrates an example apparatus 600 that may be configured to perform the tasks described herein. As shown, apparatus 600 may include a processor (e.g., one or more processors) 602, which may be a central processing unit (CPU), a graphics processing unit (GPU), a microcontroller, a reduced instruction set computer (RISC) processor, application specific integrated circuits (ASICs), an application-specific instruction-set processor (ASIP), a physics processing unit (PPU), a digital signal processor (DSP), a field programmable gate array (FPGA), or any other circuit or processor capable of executing the functions described herein. Apparatus 600 may further include a communication circuit 604, a memory 606, a mass storage device 608, an input device 610, and/or a communication link 612 (e.g., a communication bus) over which the one or more components shown in the figure may exchange information.

Communication circuit 604 may be configured to transmit and receive information utilizing one or more communication protocols (e.g., TCP/IP) and one or more communication networks including a local area network (LAN), a wide area network (WAN), the Internet, a wireless data network (e.g., a Wi-Fi, 3G, 4G/LTE, or 5G network). Memory 606 may include a storage medium (e.g., a non-transitory storage medium) configured to store machine-readable instructions that, when executed, cause processor 602 to perform one or more of the functions described herein. Examples of the machine-readable medium may include volatile or non-volatile memory including but not limited to semiconductor memory (e.g., electrically programmable read-only memory (EPROM), electrically erasable programmable read-only memory (EEPROM)), flash memory, and/or the like. Mass storage device 608 may include one or more magnetic disks such as one or more internal hard disks, one or more removable disks, one or more magneto-optical disks, one or more CD-ROM or DVD-ROM disks, etc., on which instructions and/or data may be stored to facilitate the operation of processor 602. Input device 610 may include a keyboard, a mouse, a voice-controlled input device, a touch sensitive input device (e.g., a touch screen), and/or the like for receiving user inputs to apparatus 600.

It should be noted that apparatus 600 may operate as a standalone device or may be connected (e.g., networked or clustered) with other computation devices to perform the tasks described herein. And even though only one instance of each component is shown in FIG. 6, a skilled person in the art will understand that apparatus 600 may include multiple instances of one or more of the components shown in the figure.

While this disclosure has been described in terms of certain embodiments and generally associated methods, alterations and permutations of the embodiments and methods will be apparent to those skilled in the art. Accordingly, the above description of example embodiments does not constrain this disclosure. Other changes, substitutions, and alterations are also possible without departing from the spirit and scope of this disclosure. In addition, unless specifically stated otherwise, discussions utilizing terms such as "analyzing," "determining," "enabling," "identifying," "modifying" or the like, refer to the actions and processes of a computer system, or similar electronic computing device, that manipulates and transforms data represented as physical (e.g., electronic) quantities within the computer system's registers and memories into other data represented as physical quantities within the computer system memories or other such information storage, transmission or display devices.

It is to be understood that the above description is intended to be illustrative, and not restrictive. Many other implementations will be apparent to those of skill in the art upon reading and understanding the above description.

What is claimed is:

1. An apparatus, comprising:
at least one processor configured to:
obtain a three-dimensional (3D) anatomical model representing one or more blood vessels of a patient;
obtain a two-dimensional (2D) fluoroscopic image of all or a subset of the one or more blood vessels, wherein the 2D fluoroscopic image indicates that at least one of the one or more blood vessels is injected with a contrast agent;
determine, automatically and using an artificial neural network (ANN), an injection site of the contrast agent in the 2D fluoroscopic image, wherein the ANN is pre-trained to recognize image features associated with the injection site from the 2D fluoroscopic image;
determine the injection site on the 3D anatomical model; and
register the 3D anatomical model with the 2D fluoroscopic image based at least on respective locations of the injection site in the 2D fluoroscopic image and on the 3D anatomical model such that the 3D anatomical model aligns approximately with the 2D fluoroscopic image with respect to the at least one of the one or more blood vessels associated with the injection site, wherein the injection site is used as a reference landmark for registering the 3D anatomical model with the 2D fluoroscopic image.

2. The apparatus of claim 1, wherein the at least one processor is further configured to overlay the 3D anatomical model onto the 2D fluoroscopic image, and generate an image that depicts the overlaid 3D anatomical model and the 2D fluoroscopic image.

3. The apparatus of claim 2, further comprising a monitor or a virtual reality (VR) headset, wherein the at least one processor is further configured to display the image that depicts the overlaid 3D blood vessel model and the 2D fluoroscopic image on the monitor or through the VR headset.

4. The apparatus of claim 1, wherein the at least one processor is configured to determine the injection site on the 3D anatomical model based on a user input that indicates the location of the injection site on the 3D anatomical model.

5. The apparatus of claim 1, wherein the processor is configured to register the 3D anatomical model with the 2D fluoroscopic image using at least one other ANN.

6. The apparatus of claim 1, wherein the at least one processor being configured to determine the injection site on the 3D anatomical model comprises the at least one processor being configured to:
segment the 3D anatomical model into multiple segments each representing an anatomical structure of the patient;
receive a user input that indicates which one or more of the multiple segments include the injection site; and
determine the injection site on the 3D anatomical model based on the user input.

7. The apparatus of claim 1, wherein the 2D fluoroscopic image is obtained using a medical imaging device, and wherein the at least one processor being configured to determine the injection site on the 3D anatomical model comprises the at least one processor being configured to:
determine a position and a body shape of the patient based on information provided by a sensing device;
determine relative positions and orientations of the 3D anatomical model and the sensing device based on the position and body shape of the patient;
determine relative positions and orientations of the medical imaging device and the sensing device; and
determine the injection site on the 3D anatomical model based at least on the position or body shape of the patient, the relative positions and orientations of the 3D anatomical model and the sensing device, and the relative positions and orientations of the medical imaging device and the sensing device.

8. The apparatus of claim 1, wherein the at least one processor is further configured to generate, based on the 2D fluoroscopic image and a pre-trained artificial intelligence (AI) segmentation model, a 2D segmentation mask associated with the one or more blood vessels of the patient, and register the 2D segmentation mask with the 3D anatomical model based on the injection site.

9. The apparatus of claim 1, wherein the at least one processor is further configured to:
detect, based on the 2D fluoroscopic image, a medical device implanted inside one of the one or more blood vessels of the patient;
generate, based on a predefined device model, a 3D model of the medical device; and
overlay the 3D model of the medical device onto a 3D image that depicts the one of the one or more blood vessels in which the medical device is implanted.

10. The apparatus of claim 5, wherein the at least one other ANN comprises a neural ordinary differential equation network.

11. A method for medical image fusion, the method comprising:
obtaining a three-dimensional (3D) anatomical model representing one or more blood vessels of a patient;
obtaining a two-dimensional (2D) fluoroscopic image of all or a subset of the one or more blood vessels, wherein the 2D fluoroscopic image indicates that at least one of the one or more blood vessels is injected with a contrast agent;
determining, automatically and using an artificial neural network (ANN), an injection site of the contrast agent in the 2D fluoroscopic image, wherein the ANN is pre-trained to recognize image features associated with the injection site from the 2D fluoroscopic image;
determining the injection site on the 3D anatomical model; and
registering the 3D anatomical model with the 2D fluoroscopic image based at least on respective locations of the injection site in the 2D fluoroscopic image and on the 3D anatomical model such that the 3D anatomical model aligns approximately with the 2D fluoroscopic image with respect to the at least one of the one or more blood vessels associated with the injection site, wherein the injection site is used as a reference landmark for registering the 3D anatomical model with the 2D fluoroscopic image.

12. The method of claim 11, further comprising overlaying the 3D anatomical model onto the 2D fluoroscopic image, and generating an image that depicts the overlaid 3D anatomical model and the 2D fluoroscopic image.

13. The method of claim 12, further comprising displaying the image that depicts the overlaid 3D blood vessel model and the 2D fluoroscopic image on a monitor or through a virtual reality headset.

14. The method of claim 11, wherein the injection site is determined on the 3D anatomical model based on a user input that indicates the location of the injection site on the 3D anatomical model.

15. The method of claim 11, wherein the registering of the 3D anatomical model with the 2D fluoroscopic image is performed using at least one other ANN.

16. The method of claim 11, wherein determining the injection site on the 3D anatomical model comprises:
    segmenting the 3D anatomical model into multiple segments each representing an anatomical structure of the patient;
    receiving a user input that indicates which one or more of the multiple segments include the injection site; and
    determining the injection site on the 3D anatomical model based on the user input.

17. The method of claim 11, wherein the 2D fluoroscopic image is obtained using a medical imaging device, and wherein determining the injection site on the 3D anatomical model comprises:
    determine a position and a body shape of the patient based on information provided by a sensing device;
    determine relative positions and orientations of the 3D anatomical model and the sensing device based on the position and body shape of the patient;
    determine relative positions and orientations of the medical imaging device and the sensing device; and
    determine the injection site on the 3D anatomical model based at least on the position or body shape of the patient, the relative positions and orientations of the 3D anatomical model and the sensing device, and the relative positions and orientations of the medical imaging device and the sensing device.

18. The method of claim 11, further comprising generating, based on the 2D fluoroscopic image and a pre-trained artificial intelligence (AI) segmentation model, a 2D segmentation mask associated with the one or more blood vessels of the patient, and registering the 2D segmentation mask with the 3D anatomical model based on the injection site.

19. The method of claim 11, further comprising:
    detecting, based on the 2D fluoroscopic image, a medical device implanted inside one of the one or more blood vessels of the patient;
    generating, based on a predefined device model, a 3D model of the medical device; and
    overlaying the 3D model of the medical device onto a 3D image that depicts the one of the one or more blood vessels in which the medical device is implanted.

20. The method of claim 15, wherein the at least one other ANN comprises a neural ordinary differential equation network.

* * * * *